(12) United States Patent
Kargar et al.

(10) Patent No.: US 8,774,361 B2
(45) Date of Patent: Jul. 8, 2014

(54) SYSTEM FOR IDENTIFYING RADIATION ZONES IN X-RAY IMAGING

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 345 days.

(21) Appl. No.: 13/412,713

(22) Filed: Mar. 6, 2012

(65) Prior Publication Data

US 2012/0314842 A1 Dec. 13, 2012

Related U.S. Application Data

(60) Provisional application No. 61/494,922, filed on Jun. 9, 2011.

(51) Int. Cl.
*G01N 23/201* (2006.01)
(52) U.S. Cl.
USPC ............................................. 378/86; 378/204
(58) Field of Classification Search
CPC .. G01N 23/201; G01N 23/203; G01V 5/0025
USPC ............... 378/86, 98, 98.2, 162, 204
See application file for complete search history.

(56) References Cited

U.S. PATENT DOCUMENTS

| 7,907,697 B2 | 3/2011 | Maltz |
| 2007/0080308 A1 | 4/2007 | Mousavi Yeganeh |
| 2010/0046696 A1 | 2/2010 | Maltz |

OTHER PUBLICATIONS

Arizona State University, "Appendix A: Radiation Hazards of Analytical X-Ray Equipment", website http://www.asu.edu/radiationsafety/x-ray/appn__A.html, printed on Feb. 21, 2012.
Les Wilkins & Assoc., Inc., "Scatter Radiation", web site http://www.leswilkins.com/scatter.htm, printed on Feb. 21, 2012.
G McVey and H Weatherburn, "A Study of Scater in Diagnostic X-Ray Room", The British Journal of Radiology, 77 (2004), 28-38.

*Primary Examiner* — Jurie Yun
(74) *Attorney, Agent, or Firm* — Brennan K. Bradley

(57) ABSTRACT

A system displays potential radiation zones in an angiography X-ray laboratory during an angiography procedure, for example, and identifies areas of potentially harmful radiation due to X-ray scatter in an imaging room. An input processor receives data identifying an emitted X-ray dose level applied to an area of a patient anatomy. An image data processor determines level of X-ray radiation dose scatter in different regions of an imaging room indicating regions of potentially harmful radiation, by calculating X-ray scatter dose at different distances from an irradiated patient area as being substantially in proportion to the size of the irradiated area and substantially inversely proportional to the square of the distance from the irradiated area. A visual alert system visually identifies areas of a room of potentially harmful radiation in response to the determination.

24 Claims, 4 Drawing Sheets

SYSTEM FOR IDENTIFYING RADIATION ZONES IN X-RAY IMAGING

This is a non-provisional application of provisional application Ser. No. 61/494,922 filed Jun. 9, 2011, by S. Kargar et al.

FIELD OF THE INVENTION

This invention concerns a system for identifying areas of potentially harmful radiation due to X-ray scatter in an imaging room involving determining X-ray scatter radiation dose at different distances from an irradiated patient area.

BACKGROUND OF THE INVENTION

X-ray imaging equipment uses narrow collimated X-ray beams of high intensity radiation. Exposure of body parts to a primary X-ray beam may result in severe radiation burns in a matter of seconds. Exposure to scattered radiation also poses a hazard. Scattered radiation is produced when a primary X-ray beam strikes collimators, beam stops, samples or shielding. The intensity of scattered radiation is typically a couple of orders of magnitude less than that of the primary beam but is still capable of causing harm to a patient when radiation limits are exceeded.

Radiation cannot be detected by human senses. Medical personnel who work in an angiography X-ray laboratory may be exposed to a lot of scattered radiation. Although, wearing radiation safety devices (such as lead apron, radiation safety glasses) reduces the amount of radiation, this only protects certain regions of the body and the safety devices are not 100% effective. A system according to invention principles provides guidance (such as visual guidance) to medical personnel indicating location of potential radiation zones in an X-ray imaging room.

SUMMARY OF THE INVENTION

A system displays potential radiation zones in an angiography X-ray laboratory during an angiography procedure, for example, and identifies areas of potentially harmful radiation due to X-ray scatter in an imaging room. An input processor receives data identifying an emitted X-ray dose level applied to an area of a patient anatomy. An image data processor determines level of X-ray radiation dose scatter in different regions of an imaging room indicating regions of potentially harmful radiation, by calculating X-ray scatter dose at different distances from an irradiated patient area as being substantially in proportion to the size of the irradiated area and substantially inversely proportional to the square of the distance from the irradiated area. A visual alert system visually identifies areas of a room of potentially harmful radiation in response to the determination.

DETAILED DESCRIPTION OF THE INVENTION

A system displays potential radiation zones in an angiography X-ray laboratory during an angiography procedure, for example. Scattered radiation is produced by X-rays being deflected by patient anatomy, such as bone. It has been advantageously determined that the proportion and amount of the bad non-image forming scattered radiation versus the good radiation is a function primarily of the volume of anatomy being radiographed. The amount of radiation scattered into an area depends on the factors such as the level of acceleration (tube) voltage (in Kv) used, body mass index of a patient (BMI) and selected angle of a radiation detector, for example.

Figure 1:
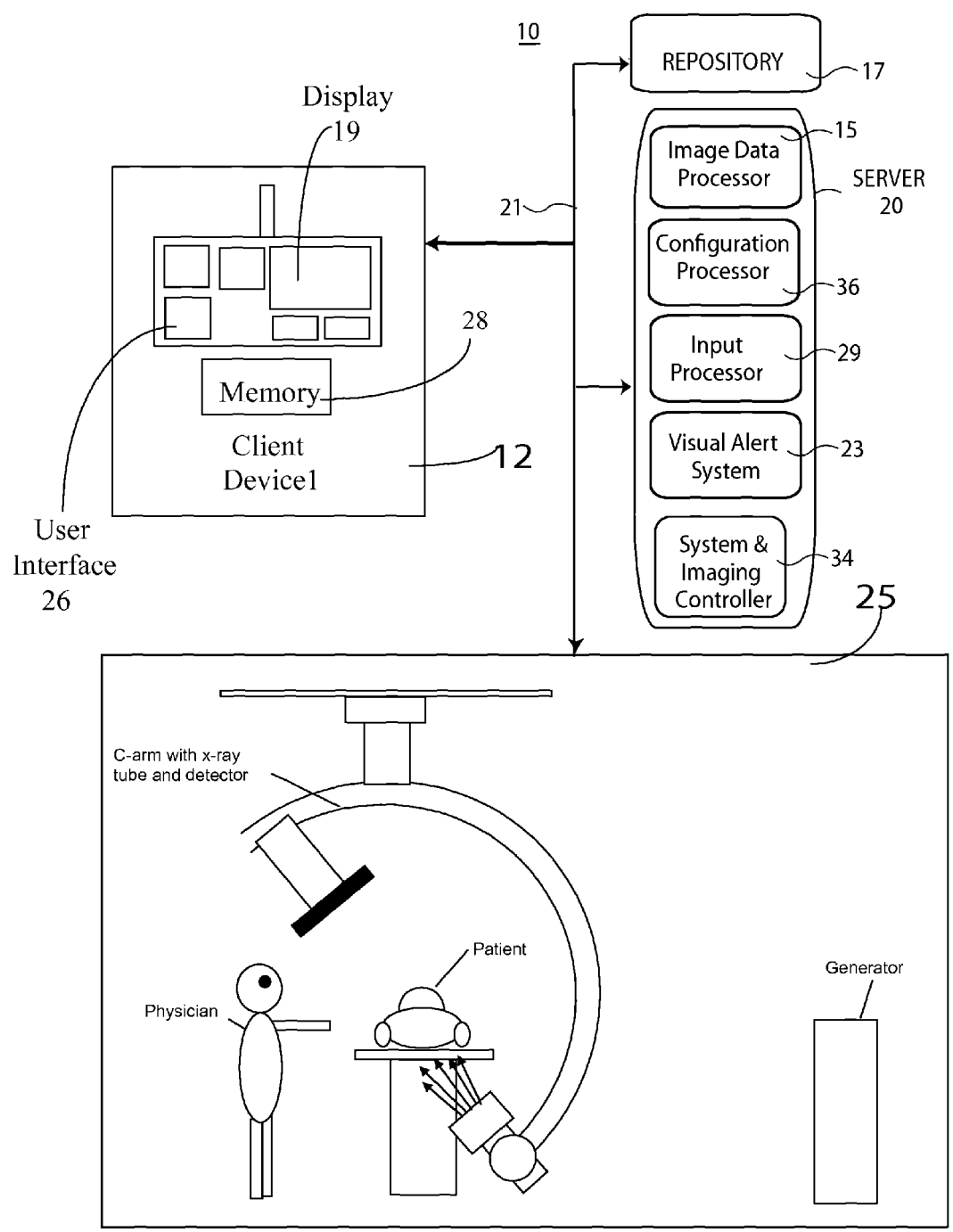
FIG. 1 shows a system for identifying areas of potentially harmful radiation due to X-ray scatter in an imaging room, according to invention principles.

FIG. 1 shows system 10 for identifying areas of potentially harmful radiation due to X-ray scatter in an imaging room. System 10 includes one or more processing devices (e.g., workstations, computers or portable devices such as notebooks, Personal Digital Assistants, phones) 12 that individually include a user interface 26 enabling user interaction with a Graphical User Interface (GUI) and display 19 supporting GUI and medical image presentation in response to predetermined user (e.g., physician) specific preferences. System 10 also includes at least one repository 17 and server (computer) 20. Server 20 includes image data processor 15, input processor 29, visual alert system 23, configuration processor 36 and system and imaging control unit 34. System and imaging control unit 34 controls operation of imaging device 25 for performing image acquisition of patient anatomy in response to user command Imaging device 25 comprise a single device (e.g., a mono-plane or biplane X-ray imaging system or computed tomography (CT) system). The units of system 10 intercommunicate via network 21. At least one repository 17 stores medical image studies for patients in DICOM compatible (or other) data format. A medical image study individually includes multiple image series of a patient anatomical portion which in turn individually include multiple images. Imaging device 25 acquires multiple sequential images (which may or may not be synchronized with ECG and respiratory signals) of a patient volume of interest. At least one repository 17 stores 2D image data or a 3D image volume dataset representing an imaging volume. Configuration processor 36 supports user configuration of system parameters.

Input processor 29 receives data identifying an emitted X-ray dose level applied to an area of a patient anatomy. Image data processor 15 determines level of X-ray radiation dose scatter in different regions of an imaging room indicating regions of potentially harmful radiation, by calculating X-ray scatter dose at different distances from an irradiated patient area as being substantially in proportion to the size of the irradiated area and substantially inversely proportional to the square of the distance from the irradiated area. Visual alert system 23 visually identifies areas of a room of potentially harmful radiation in response to the determination. Image data processor 15 calculates a factor indicating proportion of the emitted X-ray dose scattered at a particular distance from the irradiated area. The factor is calculated as being substantially in proportion to the size of the irradiated area and substantially inversely proportional to the square of the distance from the irradiated area.

Medical personnel who work in an X-ray examination imaging room during an imaging procedure are at a high risk of being exposed to scattered radiation. System 10 minimizes the risk of exposure by providing a visual indication of the location of potential scattered X-ray radiation. The system calculates an approximate area of scattered radiation using angulations and rotational angles of a radiation detector, body mass index (BMI) of a patient and a patient body part being X-rayed, and level of X-ray tube voltage (Kv) used, for example. The system visually identifies the radiation zones of potential scattered radiation in an Examination imaging room so that personnel are able to know a location of scattered radiation and can avoid the area if possible (e.g. when they need to work close to an X-ray table to set up the a contrast agent injector for injecting contrast media).

Figure 2:
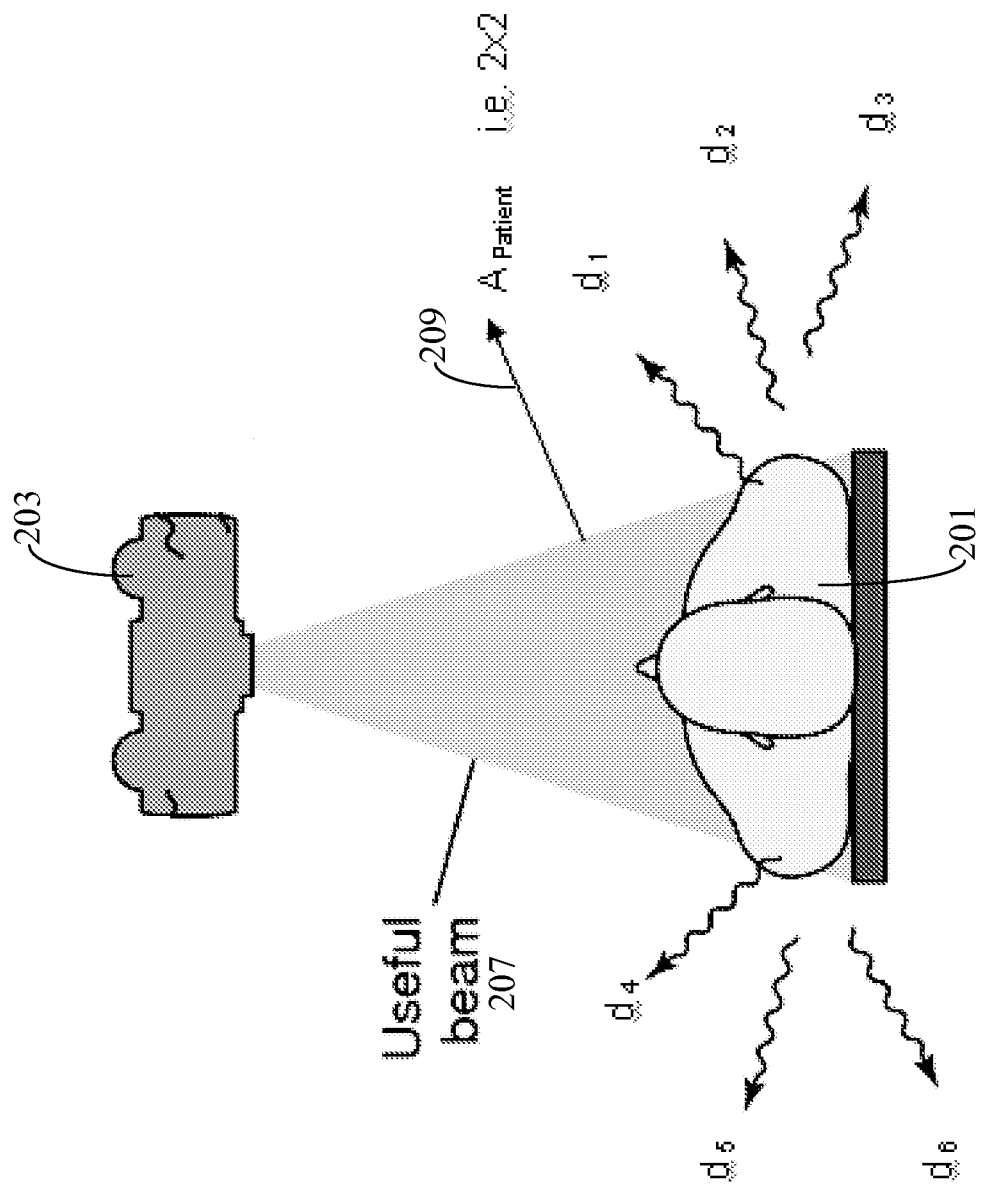
FIG. 2 illustrates calculation of radiation scatter at different distances and different directions, according to invention principles.

FIG. 2 illustrates calculation of radiation scattered in different directions from an irradiated area of a patient and at different distances from the irradiated area. A cone shaped radiation beam 207 from radiation source 203 irradiates an area ($A_{patient}$) of patient 201 which comprises a 2×2 inch area, for example. Radiation is scattered in multiple directions as illustrated by vectors d1, d2, d3, d4, d5, d6. In one embodiment the system advantageously determines a proportion S (e.g., a percentage) of emitted radiation (E) from source 203 comprising scattered radiation from the irradiated patient area $A_{patient}$ (square inches) for a delivered radiation dose at a distance d (inches) from the irradiated area using, $$S=100(A_{patient}/100)*(0.0005/d^2)$$

Where radiation proportion S is the proportion of the emitted Dose (E) from source 203 and emitted dose is in Gray units Gy, for example, so scattered dose (Y) is $$Y=S*E(\text{emitted Dose}).$$

In an example, $A_{patient}=2\times2=4$ inches$^2$, d=20 inches and $$S=100(4/100)*(0.0005/400)=0.000005$$

Therefore, scattered radiation 209 is S=0.000005 Gy.

The amount of radiation scattered into an area depends on E (emitted Dose) of an X-ray imaging system. E is determined in response to, level of acceleration (tube) voltage (in Kv), an angle of emission of X-ray radiation from a radiation source and a parameter associated with a patient dimension and mass such as BMI (Body Mass Index or weight and height, for example). The tube voltage (Kv) and associated acceleration current (mA) are calculated based on patient transparency to X-ray radiation (BMI) and angle of radiation beam projection relative to an irradiated patient skin surface.

Figure 3:
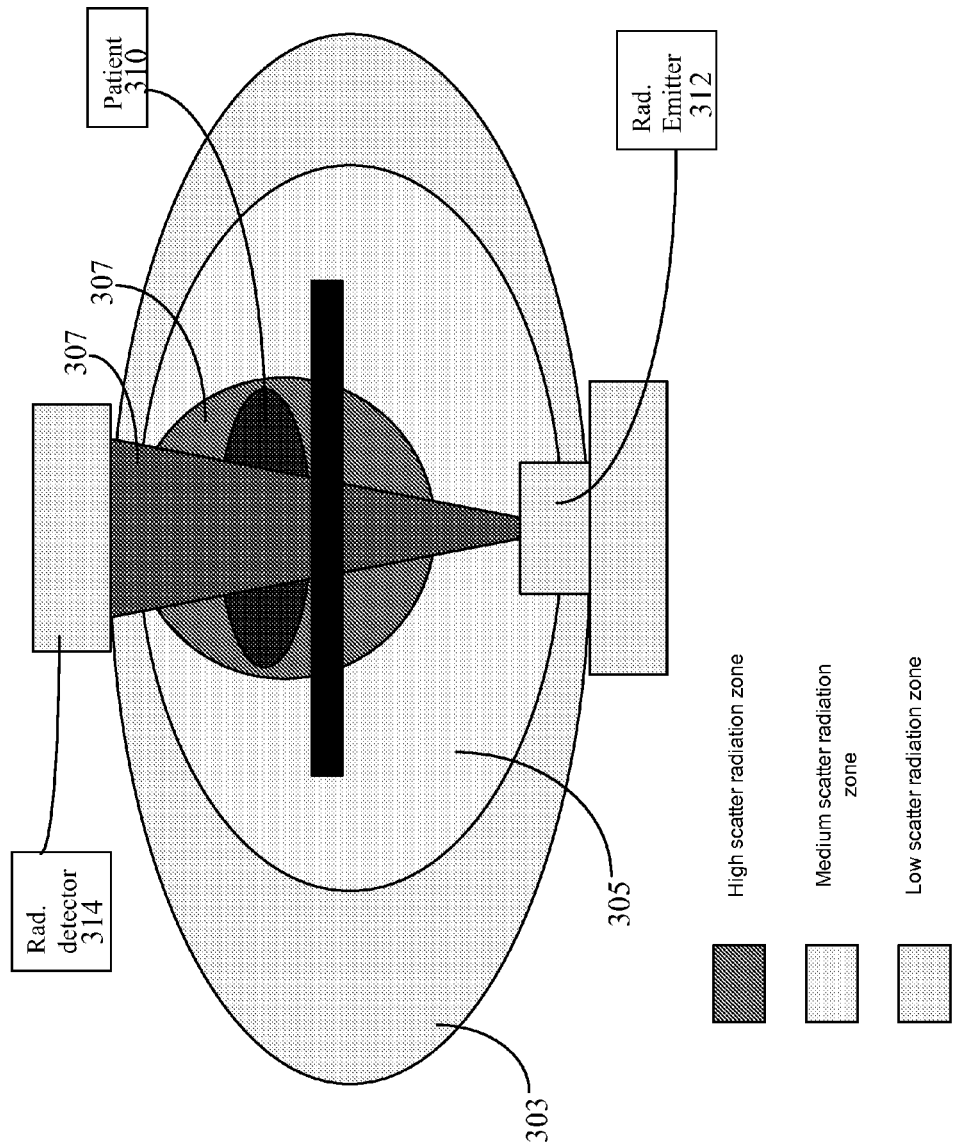
FIG. 3 shows a diagram of radiation zones of different severity level provided to an X-ray imaging system user, according to invention principles.

FIG. 3 shows a diagram of radiation zones of different severity level provided to an X-ray imaging system user. Visual alert system 23 (FIG. 1) visually identifies areas of a room of potentially harmful radiation in response to calculation of proportion S of emitted radiation (E) from source 312 (FIG. 3) comprising scattered radiation from an irradiated patient area $A_{patient}$ for a delivered radiation dose at a range of different distances d and a range of different angles from the irradiated patient area. The diagram shows calculated radiation zones of high scattered radiation 307, medium scattered radiation 305 and low scattered radiation 303 as well as the patient zone 310. Non-scattered radiation from source 312 passes through a patient in zone 310 and is detected by radiation detector 314.

System 10 is usable with different types of X-ray equipment including C-arm X-ray imaging systems and CT scanning systems. Further, the system employs configurable thresholds discriminating between the high, medium and low scattered radiation zones. The radiation zones vary in response to factors including X-ray tube voltage, BMI of a patient and angle of radiation detector. The system further enables configuration of a desired accuracy of zone boundary detection. A Graphical User Interface (GUI) provided by user interface 26, comprises display images enabling user data entry for configuring system parameters by configuration processor 36.

Visual alert system 23 advantageously provides a visual alert to medical personnel identifying relative radiation intensity level and associated location of individual zones in an angiography X-ray laboratory. In one embodiment system 10 is incorporated within an angiography X-ray imaging system. The potential radiation zones are identified via visual or other attributes. The system advantageously visually identifies the radiation zones of potential scattered radiation in an Examination imaging room so that personnel are able to know the location of scattered radiation zones of differing levels of radiation intensity. Thereby personnel working within a radiation examination imaging room can avoid zones of higher levels of scattered radiation intensity. A user may need to work in an examination imaging room when it is necessary to work close to an X-ray system patient support table in order to set up a contrast agent injector for injecting contrast agent into a patient, for example.

In one embodiment, visual alert system 23 visually identifies areas of an examination imaging room using visual indicators in a room activated in response to the determination. The visual indicators comprise, lights, signs, indicator strips that are illuminated or colored, LEDs, projected light beams or another type of indicator. In another embodiment, visual alert system 23 visually identifies regions of the imaging room having potentially harmful levels of X-ray scatter radiation in a display image comprising a visual representation of the imaging room. The visual representation of the imaging room comprises at least one of a 3D (three dimensional) and a 2D (two dimensional) representation, showing the room in a plan view from above or below and indicating at least one region of potentially harmful X-ray radiation scatter. Alternatively, the imaging room representation shows the room in a side view indicating at least one region of potentially harmful X-ray radiation scatter. The visual alert system indicates multiple different regions of potentially harmful radiation in the visual representation of the imaging room and associated radiation intensity level, by visual attribute such as color, shading, highlighting, text or symbol, for example.

Figure 4:
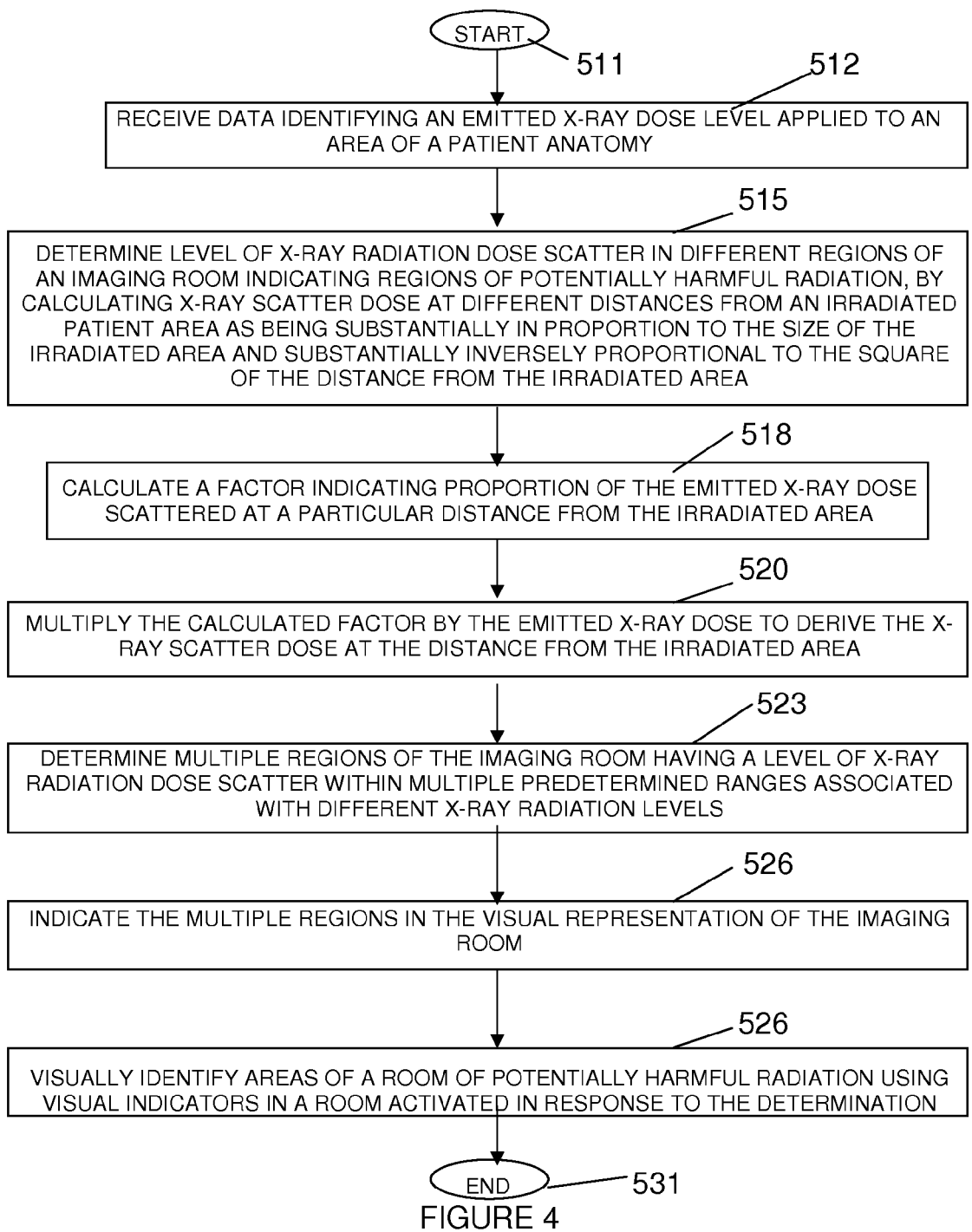
FIG. 4 shows a flowchart of a process performed by a system for identifying areas of potentially harmful radiation due to X-ray scatter in an imaging room, according to invention principles.

FIG. 4 shows a flowchart of a process performed by system 10 (FIG. 1) for identifying areas of potentially harmful radiation due to X-ray scatter in an imaging room. Input processor 29 in step 512 following the start at step 511, receives data identifying an emitted X-ray dose level applied to an area of a patient anatomy. In step 515 image data processor 15 determines level of X-ray radiation dose scatter in different regions of an imaging room indicating regions of potentially harmful radiation, by calculating X-ray scatter dose at different distances from an irradiated patient area as being substantially in proportion to the size of the irradiated area and substantially inversely proportional to the square of the distance from the irradiated area. The irradiated area comprises a patient body skin surface area or an internal anatomical area. Processor 15 in step 518, calculates a factor indicating proportion of the emitted X-ray dose scattered at a particular distance from the irradiated area. The factor is calculated as being substantially in proportion to the size of the irradiated area and substantially inversely proportional to the square of the distance from the irradiated area.

Processor 15 in step 520 multiplies the calculated factor by the emitted X-ray dose to derive the X-ray scatter dose at the distance from the irradiated area. The emitted X-ray dose level applied to an area of a patient anatomy is determined by at least two of, (a) an angle of emission of X-ray radiation from a radiation source, (b) an X-ray emission tube voltage and (c) a parameter associated with a patient dimension and mass comprising at least one of, body mass index, patient circumference and patient cross sectional area. In step 523 processor 15 determines multiple regions of the imaging room having a level of X-ray radiation dose scatter within multiple predetermined ranges associated with different X-ray radiation levels. Processor 15 determines a region of the imaging room having a level of X-ray radiation dose scatter within a predetermined range associated with a potentially harmful X-ray radiation level. In step 526 visual alert system 23 indicates the multiple regions in the visual representation of the imaging room. In step 526 visual alert system 23 visually identifies areas of a room of potentially harmful radiation in response to the determination. In one embodiment system 23 visually identifies regions of the imaging room having potentially harmful levels of X-ray scatter radiation in a display image comprising a visual representation of the imaging room. The visual representation of the imaging room comprises at least one of a 3D (three dimensional) and a 2D (two dimensional) representation, showing the room in a plan view from above or below and indicating at least one region of potentially harmful X-ray radiation scatter. In another embodiment, system 23 visually identifies areas of a room using visual indicators (lights, signs, for example) in a room activated in response to the determination. The process of FIG. 4 terminates at step 531.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command An activity (including a step) performed automatically is performed in response to executable instruction or device operation without user direct initiation of the activity.

The system and processes of FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system visually identifies potential scattered radiation zones in an angiography X-ray laboratory during an angiography procedure, in response to factors including acceleration (tube) voltage used, body mass index of a patient (BMI) and selected angle of a radiation detector, for example. Further, the processes and applications may, in alternative embodiments, be located on one or more (e.g., distributed) processing devices on a network linking the units of FIG. 1. Any of the functions and steps provided in FIGS. 1-4 may be implemented in hardware, software or a combination of both.

What is claimed is:

1. A system for identifying areas of potentially harmful radiation due to X-ray scatter in an imaging room, comprising:
    an input processor for receiving data identifying an emitted X-ray dose level applied to an area of a patient anatomy;
    an image data processor for determining level of X-ray radiation dose scatter in different regions of an imaging room indicating regions of potentially harmful radiation, by calculating X-ray scatter dose at different distances from an irradiated patient area as being substantially in proportion to the size of the irradiated area and substantially inversely proportional to the square of the distance from the irradiated area; and
    a visual alert system for visually identifying areas of the room of potentially harmful radiation in response to the determination.

2. A system according to claim 1, wherein
    said image data processor calculates a factor indicating proportion of said emitted X-ray dose scattered at a particular distance from said irradiated area, said factor being calculated as being substantially in proportion to the size of the irradiated area and substantially inversely proportional to the square of said distance from the irradiated area.

3. A system according to claim 2, wherein
said image data processor multiplies the calculated factor by said emitted X-ray dose level to derive the X-ray scatter dose at said distance from the irradiated area.

4. A system according to claim 2, wherein
said irradiated area comprises a patient body skin surface area.

5. A system according to claim 2, wherein
said irradiated area comprises an internal anatomical area.

6. A system according to claim 1, wherein
said visual alert system visually identifies regions of the imaging room having potentially harmful levels of X-ray scatter radiation in a display image comprising a visual representation of the imaging room.

7. A system according to claim 6, wherein
said visual representation of the imaging room comprises at least one of a 3D (three dimensional) and a 2D (two dimensional) representation, showing the room in a plan view from above or below and indicating at least one region of potentially harmful X-ray radiation scatter.

8. A system according to claim 6, wherein
said image data processor determines a region of said imaging room having a level of X-ray radiation dose scatter within a predetermined range associated with a potentially harmful X-ray radiation level and
said visual alert system indicates said region of potentially harmful radiation in said visual representation of the imaging room.

9. A system according to claim 8, wherein
said image data processor determines a plurality of regions of said imaging room having a level of X-ray radiation dose scatter within a plurality of predetermined ranges associated with different X-ray radiation levels and
said visual alert system indicates said plurality of regions in said visual representation of the imaging room.

10. A system according to claim 1, wherein
said visual alert system visually identifies areas of the room using visual indicators in the room activated in response to the determination.

11. A system according to claim 1, wherein
said emitted X-ray dose level applied to an area of a patient anatomy is determined by at least two of, (a) an angle of emission of X-ray radiation from a radiation source, (b) an X-ray emission tube voltage and (c) a parameter associated with a patient dimension and mass.

12. A system according to claim 11, wherein
said parameter associated with a patient dimension and mass comprises at least one of, (a) body mass index, (b) patient circumference and (c) patient cross sectional area.

13. A method for identifying areas of potentially harmful radiation due to X-ray scatter in an imaging room, comprising the steps of:
receiving data identifying an emitted X-ray dose level applied to an area of a patient anatomy;
determining level of X-ray radiation dose scatter in different regions of an imaging room indicating regions of potentially harmful radiation, by calculating X-ray scatter dose at different distances from an irradiated patient area as being substantially in proportion to the size of the irradiated area and substantially inversely proportional to the square of the distance from the irradiated area; and
visually identifying areas of the room of potentially harmful radiation in response to the determination.

14. A method according to claim 13, including the step of calculating a factor indicating proportion of said emitted X-ray dose scattered at a particular distance from said irradiated area, said factor being calculated as being substantially in proportion to the size of the irradiated area and substantially inversely proportional to the square of said distance from the irradiated area.

15. A method according to claim 14, including the step of multiplying the calculated factor by said emitted X-ray dose level to derive the X-ray scatter dose at said distance from the irradiated area.

16. A method according to claim 14, wherein
said irradiated area comprises a patient body skin surface area.

17. A method according to claim 14, wherein
said irradiated area comprises an internal anatomical area.

18. A method according to claim 13, including the step of visually identifying regions of the imaging room having potentially harmful levels of X-ray scatter radiation in a display image comprising a visual representation of the imaging room.

19. A method according to claim 18, wherein
said visual representation of the imaging room comprises at least one of a 3D (three dimensional) and a 2D (two dimensional) representation, showing the room in a plan view from above or below and indicating at least one region of potentially harmful X-ray radiation scatter.

20. A method according to claim 18, including the steps of determining a region of said imaging room having a level of X-ray radiation dose scatter within a predetermined range associated with a potentially harmful X-ray radiation level and
indicating said region of potentially harmful radiation in said visual representation of the imaging room.

21. A method according to claim 20, including the steps of determining a plurality of regions of said imaging room having a level of X-ray radiation dose scatter within a plurality of predetermined ranges associated with different X-ray radiation levels and
indicating said plurality of regions in said visual representation of the imaging room.

22. A method according to claim 13, including the step of visually identifying areas of the room using visual indicators in the room activated in response to the determination.

23. A method according to claim 13, wherein
said emitted X-ray dose level applied to an area of a patient anatomy is determined by at least two of, (a) an angle of emission of X-ray radiation from a radiation source, (b) an X-ray emission tube voltage and (c) a parameter associated with a patient dimension and mass.

24. A method according to claim 23, wherein
said parameter associated with a patient dimension and mass comprises at least one of, (a) body mass index, (b) patient circumference and (c) patient cross sectional area.

* * * * *